(12) United States Patent
Wilmer et al.

(10) Patent No.: US 7,459,607 B2
(45) Date of Patent: Dec. 2, 2008

(54) OIL BIOSYNTHESIS

(75) Inventors: Jeroen Alexander Wilmer, Cambridge (GB); Emma Jane Wallington, Cambridge (GB); Antoni Ryszard Slabas, Durham (GB)

(73) Assignee: BIOGEMMA UK Limited, Cambridgeshire (GB)

( * ) Notice: Subject to any disclaimer, the term of this patent is extended or adjusted under 35 U.S.C. 154(b) by 342 days.

(21) Appl. No.: 10/492,221

(22) PCT Filed: Oct. 11, 2002

(86) PCT No.: PCT/GB02/04642

§ 371 (c)(1),
(2), (4) Date: Jan. 21, 2005

(87) PCT Pub. No.: WO03/033713

PCT Pub. Date: Apr. 24, 2003

(65) Prior Publication Data

US 2005/0125858 A1    Jun. 9, 2005

(30) Foreign Application Priority Data

Oct. 12, 2001 (GB) .................. 0124574.5

(51) Int. Cl.
*A01H 5/00*       (2006.01)
*C12N 15/82*      (2006.01)
(52) U.S. Cl. ..................... 800/306; 800/281
(58) Field of Classification Search ............ None
See application file for complete search history.

(56) References Cited

U.S. PATENT DOCUMENTS

| 5,968,791 | A | * | 10/1999 | Davies et al. | ............ 435/134 |
| 6,051,755 | A |   | 4/2000  | Zou et al.    | ............ 800/281 |

FOREIGN PATENT DOCUMENTS

| EP | 0116718  | 8/1984  |
| EP | 0242246  | 10/1987 |
| EP | 0255278  | 2/1988  |
| EP | 0255378  | 2/1988  |
| EP | 0270822  | 6/1988  |
| EP | 0369637  | 5/1990  |
| GB | 2197653  | 5/1988  |
| WO | 9515387  | 6/1995  |
| WO | 9527791  | 10/1995 |
| WO | 9609394  | 3/1996  |
| WO | 9613582  | 5/1996  |
| WO | 9624674  | 8/1996  |
| WO | WO0129238 | 4/2001 |

OTHER PUBLICATIONS

Rossak et al. (2001) "Expression of the FAE1 gene and FAE1 promoter activity in developing seeds of *Arabidopsis thaliana*", Plant Molecular Biology 46: 717-725.

Han et al. (2001) "Functional characterization of β-ketoacyl-CoA synthase genes from *Brassica napus* L.", Plant Molecular Biology 46: 229-239.

Katavic et al. (2001) "Improving erucic acid content in rapeseed through biotechnology: what can the *Arabidopsis* FAE1 and yeast SLC1-1 genes contribute?", Crop. Sci. 41: 739-747.

Katavic et al. (2000) "Biotechnological aspects: fatty acids", Biochemical Society Transactions 28: 935-937.

Delseny et al. (1999) "Le colza érucique: problèmes et perspectives scientifiques", Fondamental 6 428-434.

Domergue et al. (1999) "Les acyl-CoA élongases des graines: l'autre système de synthèse d'acide gras", Fondamental 6: 101-106.

Ramli et al. (1998) "Flux analysis applied to oil accumulation", Advances in Plate Lipid Research 219-221.

Altschul et al. (1997) "Gapped BLAST and PSI-BLAST: a new generation of protein database search programs", Nucleic Acids Research 25: 3389-3402.

Millar et al. (1997) "Very-long-chain fatty biosynthesis is controlled through the expression and specificity of the condensing enzyme", The Plant Journal 12: 121-131.

Barret et al. (1997) "A rapeseed FAE1 gene is linked to the E! locus associated with variation in the content of erucic acid": 177-186.

Genbank Accession No. AF009563, submitted Jun. 19, 1997.

Wilmer et al. (1996) "Effect of growth temperature on erucic acid levels in seeds and microspore-derived embryos of oilseed rape, *Brassica napus* L.", J. Plant Physiol., 147: 486-492.

Brough et al. (1996) "Towards the genetic engineering of triacylglycerols of defined fatty acid composition: major changes in erucic acid content at the sn-2 position affected by the introduction of a 1-acyl-sn-glycerol-3-phosphate acyltransferase from *Limnanthes douglasii* into oil seed rape" Molecular Breeding 2: 133-142.

Lassner et al. (1996) "A jojoba β-Ketoacyl-CoA synthase cDNA complements the canola fatty acid elongation mutation in transgenic plants", The Palnt Cell 8: 281-292.

Genbank Accession No. BNU50771, submitted Mar. 6, 1996.

Ohlrogge et al. (1995) "Lipid Biosynthesis", The Plant Cell 7: 957-970.

Evenson et al. (1995) "Fatty acid-elongating activity in rapidly expanding leek epidermis", Plant Physiol., 109: 707-716.

Plant et al. (1994) Regulation of an *Arabidopsis* oleosin gene promoter in transgenic *Brassica napus*, Plant Molecular Biology 25: 193-205.

Henikoff et al. (1992) "Amino acid substitution matrices from protein blocks", Proc. Natl. Acad. Sci. USA 89: 10915-10919.

Altschul et al. (1990) "Basic local alignment search tool", J. Mol. Biol. 215: 403-410.

Moloney et al. (1989) "High efficiency transformation of *Brassica napus* using Agrobacterium vectors", Plant Cell Reports 8: 238-242.

Pearson et al. (1988) "Improved tools for biological sequence comparison", Proc. Natl. Acad. Sci. 85: 2444-2448.

(Continued)

*Primary Examiner*—Elizabeth F McElwain
(74) *Attorney, Agent, or Firm*—Baker Botts L.L.P.

(57) ABSTRACT

The invention provides a method of producing, in a plant, oil having an erucic acid content above 66% erucic acid, the method comprising (i) expressing in the plant nucleic acid encoding an elongase and nucleic acid encoding an acyltransferase enzyme; and (ii) extracting oil from the plant. Corresponding plants seeds and oils are also provided.

10 Claims, 10 Drawing Sheets

OTHER PUBLICATIONS

V.C. Knauf (1987) "The application of genetic engineering to oilseed crops", TIBTECH 5: 40-47.

Devereux et al. (1984) "A comprehensive set of sequence analysis programs for the VAX", Nucleic Acids Research 12: 387-395.

T.F. Smith (1981) "Comparison of biosequences", Advances in Aplied Mathematics 2: 482-489.

Needleman et al. (1970) "A general method applicable to the search for similarities in the amino acids sequence of two proteins", J. Mol. Biol. 48: 443-453.

Zou et al., "Modification Of Seed Oil Content And Acyl Composition In The Brassicaceae By Expression Of A Yeast sn-2 Acyltransferase Gene," The Plant Cell. Jun. 1997; vol. 9:909-923.

* cited by examiner

Figure 1

Sequence of the coding region of the Brassica napus FAE1-1 gene

```
  1   ATGACGTCCA TTAACGTAAA GCTCCTTTAC CATTACGTCA TAACCAACCT
      TACTGCAGGT AATTGCATTT CGAGGAAATG GTAATGCAGT ATTGGTTGGA

51   TTTCAACCTT TGTTTCTTTC CATTAACGGC GATCGTCGCC GGAAAAGCCT
      AAAGTTGGAA ACAAAGAAAG GTAATTGCCG CTAGCAGCGG CCTTTTCGGA

101   ATCGGCTTAC CATAGACGAT CTTCACCACT TATACTATTC CTATCTCCAA
      TAGCCGAATG GTATCTGCTA GAAGTGGTGA ATATGATAAG GATAGAGGTT

151   CACAACCTCA TAACCATTGC TCCACTCTTT GCCTTCACCG TTTTCGGTTC
      GTGTTGGAGT ATTGGTAACG AGGTGAGAAA CGGAAGTGGC AAAAGCCAAG

201   GGTTCTCTAC ATCGCAACCC GGCCCAAACC GGTTTACCTC GTTGAGTACT
      CCAAGAGATG TAGCGTTGGG CCGGGTTTGG CCAAATGGAG CAACTCATGA

251   CATGCTACCT TCCACCAACG CATTGTAGAT CAAGTATCTC CAAGGTCATG
      GTACGATGGA AGGTGGTTGC GTAACATCTA GTTCATAGAG GTTCCAGTAC

301   GATATCTTTT ACCAAGTAAG AAAAGCTGAT CCTTCTCGGA ACGGCACGTG
      CTATAGAAAA TGGTTCATTC TTTTCGACTA GGAAGAGCCT TGCCGTGCAC

351   CGATGACTCG TCCTGGCTTG ACTTCTTGAG GAAGATTCAA GAACGTTCAG
      GCTACTGAGC AGGACCGAAC TGAAGAACTC CTTCTAAGTT CTTGCAAGTC

401   GTCTAGGCGA TGAAACCCAC GGGCCCGAGG GGCTGCTTCA GGTCCCTCCC
      CAGATCCGCT ACTTTGGGTG CCCGGGCTCC CCGACGAAGT CCAGGGAGGG

451   CGGAAGACTT TTGCGGCGGC GCGTGAAGAG ACGGAGCAAG TTATCATTGG
      GCCTTCTGAA AACGCCGCCG CGCACTTCTC TGCCTCGTTC AATAGTAACC

501   TGCGCTAGAA AATCTATTCA AGAACACCAA TGTTAACCCT AAAGATATAG
      ACGCGATCTT TTAGATAAGT TCTTGTGGTT ACAATTGGGA TTTCTATATC

551   GTATACTTGT GGTGAACTCA AGCATGTTTA ATCCAACTCC TTCGCTCTCC
      CATATGAACA CCACTTGAGT TCGTACAAAT TAGGTTGAGG AAGCGAGAGG

601   GCGATGGTCG TTAACACTTT CAAGCTCCGA AGCAACGTAA GAAGCTTTAA
      CGCTACCAGC AATTGTGAAA GTTCGAGGCT TCGTTGCATT CTTCGAAATT

651   CCTTGGTGGC ATGGGTTGTA GTGCCGGCGT TATAGCCATT GATCTAGCAA
      GGAACCACCG TACCCAACAT CACGGCCGCA ATATCGGTAA CTAGATCGTT

701   AGGACTTGTT GCATGTCCAT AAAAATACGT ATGCTCTTGT GGTGAGCACA
      TCCTGAACAA CGTACAGGTA TTTTTATGCA TACGAGAACA CCACTCGTGT

751   GAGAACATCA CTTATAACAT TTACGCTGGT GATAATAGGT CCATGATGGT
      CTCTTGTAGT GAATATTGTA AATGCGACCA CTATTATCCA GGTACTACCA

801   TTCAAATTGC TTGTTCCGTG TTGGTGGGGC CGCTATTTTG CTCTCCAACA
      AAGTTTAACG AACAAGGCAC AACCACCCCG GCGATAAAAC GAGAGGTTGT
```

Figure 1, continued

```
 851   AGCCTAGAGA TCGTAGACGG TCCAAGTACG AGCTAGTTCA CACGGTTCGA
       TCGGATCTCT AGCATCTGCC AGGTTCATGC TCGATCAAGT GTGCCAAGCT

901   ACGCATACCG GAGCTGACGA CAAGTCTTTT CGTTGCGTGC AACAAGGAGA
       TGCGTATGGC CTCGACTGCT GTTCAGAAAA GCAACGCACG TTGTTCCTCT

951   CGATGAGAAC GGCAAAACCG GAGTGAGTTT GTCCAAGGAC ATAACCGATG
       GCTACTCTTG CCGTTTTGGC CTCACTCAAA CAGGTTCCTG TATTGGCTAC

1001   TTGCTGGTCG AACGGTTAAG AAAAACATAG CAACGCTGGG TCCGTTGATT
       AACGACCAGC TTGCCAATTC TTTTTGTATC GTTGCGACCC AGGCAACTAA

1051   CTTCCGTTAA GCGAGAAACT TCTTTTTTTC GTTACCTTCA TGGGCAAGAA
       GAAGGCAATT CGCTCTTTGA AGAAAAAAAG CAATGGAAGT ACCCGTTCTT

1101   ACTTTTCAAA GACAAAATCA AACATTATTA CGTCCCGGAC TTCAAGCTTG
       TGAAAAGTTT CTGTTTTAGT TTGTAATAAT GCAGGGCCTG AAGTTCGAAC

1151   CTATCGACCA TTTTGTATA CATGCCGGAG GCAAAGCCGT GATTGATGTG
       GATAGCTGGT AAAAACATAT GTACGGCCTC CGTTTCGGCA CTAACTACAC

1201   CTAGAGAAGA ACCTAGGCCT AGCACCGATC GATGTAGAGG CATCAAGATC
       GATCTCTTCT TGGATCCGGA TCGTGGCTAG CTACATCTCC GTAGTTCTAG

1251   AACGTTACAT AGATTTGGAA ACACTTCATC TAGCTCAATA TGGTATGAGT
       TTGCAATGTA TCTAAACCTT TGTGAAGTAG ATCGAGTTAT ACCATACTCA

1301   TGGCATACAT AGAAGCAAAA GGAAGGATGA AGAAAGGTAA TAAAGTTTGG
       ACCGTATGTA TCTTCGTTTT CCTTCCTACT TCTTTCCATT ATTTCAAACC

1351   CAGATTGCTT TAGGGTCAGG CTTTAAGTGT AACAGTGCAG TTTGGGTGGC
       GTCTAACGAA ATCCAGTCC GAAATTCACA TTGTCACGTC AAACCCACCG

1401   TCTAAACAAT GTCAAAGCTT CAACAAATAG TCCTTGGGAA CACTGCATCG
       AGATTTGTTA CAGTTTCGAA GTTGTTTATC AGGAACCCTT GTGACGTAGC

1451   ACAGATACCC GGTTAAAATT GATTCTGATT CAGGTAAGTC AGAGACTCGT
       TGTCTATGGG CCAATTTTAA CTAAGACTAA GTCCATTCAG TCTCTGAGCA

1501   GTCCAAAACG GTCGGTCCTA A
       CAGGTTTTGC CAGCCAGGAT T
```

Figure 2

Sequence of the coding region of the Brassica napus FAE1-2 gene

```
  1   ATGACGTCCA TTAACGTAAA GCTCCTTTAC CATTACGTCA TAACCAACCT
      TACTGCAGGT AATTGCATTT CGAGGAAATG GTAATGCAGT ATTGGTTGGA

51   TTTCAACCTT TGCTTCTTTC CGTTAACGGC GATCGTCGCC GGAAAAGCCT
      AAAGTTGGAA ACGAAGAAAG GCAATTGCCG CTAGCAGCGG CCTTTTCGGA

101   ATCGGCTTAC CATAGACGAT CTTCACCACT TATACTATTC CTATCTCCAA
      TAGCCGAATG GTATCTGCTA GAAGTGGTGA ATATGATAAG GATAGAGGTT

151   CACAACCTCA TAACCATCGC TCCACTCTTT GCCTTCACCG TTTTCGGTTC
      GTGTTGGAGT ATTGGTAGCG AGGTGAGAAA CGGAAGTGGC AAAAGCCAAG

201   GGTTCTCTAC ATCGCAACCC GGCCCAAACC GGTTTACCTC GTTGAGTACT
      CCAAGAGATG TAGCGTTGGG CCGGGTTTGG CCAAATGGAG CAACTCATGA

251   CATGCTACCT TCCACCAACG CATTGTAGAT CAAGTATCTC CAAGGTCATG
      GTACGATGGA AGGTGGTTGC GTAACATCTA GTTCATAGAG GTTCAGTAC

301   GATATCTTTT ATCAAGTAAG AAAAGCTGAT CCTTCTCGGA ACGGCACGTG
      CTATAGAAAA TAGTTCATTC TTTTCGACTA GGAAGAGCCT TGCCGTGCAC

351   CGATGACTCG TCGTGGCTTG ACTTCTTGAG GAAGATTCAA GAACGTTCAG
      GCTACTGAGC AGCACCGAAC TGAAGAACTC CTTCTAAGTT CTTGCAAGTC

401   GTCTAGGCGA TGAAACTCAC GGGCCCGAGG GGCTGCTTCA GGTCCCTCCC
      CAGATCCGCT ACTTTGAGTG CCCGGGCTCC CCGACGAAGT CCAGGGAGGG

451   CGGAAGACTT TTGCGGCGGC GCGTGAAGAG ACGGAGCAAG TTATCATTGG
      GCCTTCTGAA AACGCCGCCG CGCACTTCTC TGCCTCGTTC AATAGTAACC

501   TGCACTAGAA AATCTATTCA AGAACACCAA CGTTAACCCT AAAGATATAG
      ACGTGATCTT TTAGATAAGT TCTTGTGGTT GCAATTGGGA TTTCTATATC

551   GTATACTTGT GGTGAACTCA AGCATGTTTA ATCCAACTCC ATCGCTCTCC
      CATATGAACA CCACTTGAGT TCGTACAAAT TAGGTTGAGG TAGCGAGAGG

601   GCGATGGTCG TTAACACTTT CAAGCTCCGA AGCAACGTAA GAAGCTTTAA
      CGCTACCAGC AATTGTGAAA GTTCGAGGCT TCGTTGCATT CTTCGAAATT

651   CCTTGGTGGC ATGGGTTGTA GTGCCGGCGT TATAGCCATT GATCTAGCAA
      GGAACCACCG TACCCAACAT CACGGCCGCA ATATCGGTAA CTAGATCGTT

701   AGGACTTGTT GCATGTCCAT AAAAATACGT ATGCTCTTGT GGTGAGCACA
      TCCTGAACAA CGTACAGGTA TTTTTATGCA TACGAGAACA CCACTCGTGT

751   GAGAACATCA CTTATAACAT TTACGCTGGT GATAATAGGT CCATGATGGT
      CTCTTGTAGT GAATATTGTA AATGCGACCA CTATTATCCA GGTACTACCA

801   TTCAAATTGC TTGTTCCGTG TTGGTGGGGC CGCTATTTTG CTCTCCAACA
      AAGTTTAACG AACAAGGCAC AACCACCCCG GCGATAAAAC GAGAGGTTGT
```

Figure 2, continued

```
 851  AGCCTGGAGA TCGTAGACGG TCCAAGTACG AGCTAGTTCA CACGGTTCGA
      TCGGACCTCT AGCATCTGCC AGGTTCATGC TCGATCAAGT GTGCCAAGCT

901  ACGCATACCG GAGCTGACGA CAAGTCTTTT CGTTGCGTGC AACAAGGAGA
      TGCGTATGGC CTCGACTGCT GTTCAGAAAA GCAACGCACG TTGTTCCTCT

951  CGATGAGAAC GGCAAAATCG GAGTGAGTTT GTCCAAGGAC ATAACCGATG
      GCTACTCTTG CCGTTTTAGC CTCACTCAAA CAGGTTCCTG TATTGGCTAC

1001  TTGCTGGTCG AACGGTTAAG AAAAACATAG CAACGTTGGG TCCGTTGATT
      AACGACCAGC TTGCCAATTC TTTTTGTATC GTTGCAACCC AGGCAACTAA

1051  CTTCCGTTAA GCGAGAAACT TCTTTTTTTC GTTACCTTCA TGGGCAAGAA
      GAAGGCAATT CGCTCTTTGA AGAAAAAAAG CAATGGAAGT ACCCGTTCTT

1101  ACTTTTCAAA GATAAAATCA AACATTACTA CGTCCCGGAT TTCAAACTTG
      TGAAAAGTTT CTATTTTAGT TTGTAATGAT GCAGGGCCTA AAGTTTGAAC

1151  CTATTGACCA TTTTTGTATA CATGCCGGAG GCAGAGCCGT GATTGATGTG
      GATAACTGGT AAAAACATAT GTACGGCCTC CGTCTCGGCA CTAACTACAC

1201  CTAGAGAAGA ACCTAGCCCT AGCACCGATC GATGTAGAGG CATCAAGATC
      GATCTCTTCT TGGATCGGGA TCGTGGCTAG CTACATCTCC GTAGTTCTAG

1251  AACGTTACAT AGATTTGGAA ACACTTCATC TAGCTCAATA TGGTATGAGT
      TTGCAATGTA TCTAAACCTT TGTGAAGTAG ATCGAGTTAT ACCATACTCA

1301  TGGCATACAT AGAAGCAAAA GGAAGGATGA AGAAAGGTAA TAAAGTTTGG
      ACCGTATGTA TCTTCGTTTT CCTTCCTACT TCTTTCCATT ATTTCAAACC

1351  CAGATTGCTT TAGGGTCAGG CTTTAAGTGT AACAGTGCAG TTTGGGTGGC
      GTCTAACGAA ATCCCAGTCC GAAATTCACA TTGTCACGTC AAACCCACCG

1401  TCTAAACAAT GTCAAAGCTT CGACAAATAG TCCTTGGGAA CACTGCATCG
      AGATTTGTTA CAGTTTCGAA GCTGTTTATC AGGAACCCTT GTGACGTAGC

1451  ACAGATACCC GGTCAAAATT GATTCTGATT CAGGTAAGTC AGAGACTCGT
      TGTCTATGGG CCAGTTTTAA CTAAGACTAA GTCCATTCAG TCTCTGAGCA

1501  GTCCAAAACG GTCGGTCCTA A
      CAGGTTTTGC CAGCCAGGAT T
```

Figure 3

Sequence of the coding region of the LPAAT gene LAT2 from Limnanthes douglasii.

```
  1    ATGGCCAAAA CTAGAACTAG CTCTCTCCGC AACAGGAGAC AACTAAAGCC
       TACCGGTTTT GATCTTGATC GAGAGAGGCG TTGTCCTCTG TTGATTTCGG

51    GGCTGTAGCT GCTACTGCTG ATGATGATAA AGATGGGGTT TTTATGGTAT
       CCGACATCGA CGATGACGAC TACTACTATT TCTACCCCAA AAATACCATA

101    TGCTATCGTG TTTTAAAATT TTTGTTTGCT TTGCCATAGT GTTGATCACC
       ACGATAGCAC AAAATTTTAA AAACAAACGA AACGGTATCA CAACTAGTGG

151    GCGGTGGCAT GGGGACTAAT CATGGTCTTG CTCTTACCTT GGCCTTATAT
       CGCCACCGTA CCCCTGATTA GTACCAGAAC GAGAATGGAA CCGGAATATA

201    GAGGATTCGA CTAGGAAATC TATACGGCCA TATCATTGGT GGATTAGTGA
       CTCCTAAGCT GATCCTTTAG ATATGCCGGT ATAGTAACCA CCTAATCACT

251    TATGGATTTA CGGAATACCA ATAAAGATCC AAGGATCCGA GCATACAAAG
       ATACCTAAAT GCCTTATGGT TATTTCTAGG TTCCTAGGCT CGTATGTTTC

301    AAGAGGGCCA TTTATATAAG CAATCATGCA TCTCCTATCG ATGCTTTCTT
       TTCTCCCGGT AAATATATTC GTTAGTACGT AGAGGATAGC TACGAAAGAA

351    TGTTATGTGG TTGGCTCCCA TAGGCACAGT TGGTGTTGCA AAGAAAGAGG
       ACAATACACC AACCGAGGGT ATCCGTGTCA ACCACAACGT TTCTTTCTCC

401    TTATATGGTA TCCGCTGCTT GGACAACTAT ATACATTAGC CCATCATATT
       AATATACCAT AGGCGACGAA CCTGTTGATA TATGTAATCG GGTAGTATAA

451    CGCATAGATC GGTCAAACCC GGCTGCGGCT ATTCAGTCTA TGAAAGAGGC
       GCGTATCTAG CCAGTTTGGG CCGACGCCGA TAAGTCAGAT ACTTTCTCCG

501    AGTTCGTGTA ATAACCGAAA AGAATCTCTC TCTGATTATG TTTCCAGAGG
       TCAAGCACAT TATTGGCTTT TCTTAGAGAG AGACTAATAC AAAGGTCTCC

551    GAACCAGGTC GAGAGATGGG CGTTTACTTC CTTTCAAGAA GGGTTTTGTT
       CTTGGTCCAG CTCTCTACCC GCAAATGAAG GAAAGTTCTT CCCAAAACAA

601    CATCTAGCAC TTCAGTCACA TCTCCCAATA GTTCCGATGA TCCTTACAGG
       GTAGATCGTG AAGTCAGTGT AGAGGGTTAT CAAGGCTACT AGGAATGTCC

651    TACACATTTA GCATGGAGGA AAGGTACCTT CCGTGTCCGG CCAGTACCCA
       ATGTGTAAAT CGTACCTCCT TTCCATGGAA GGCACAGGCC GGTCATGGGT

701    TCACTGTCAA GTACCTTCCT CCTATAAACA CTGATGATTG GACTGTTGAC
       AGTGACAGTT CATGGAAGGA GGATATTTGT GACTACTAAC CTGACAACTG

751    AAAATCGACG ATTACGTCAA AATGATACAC GACGTCTATG TCCGCAACCT
       TTTTAGCTGC TAATGCAGTT TTACTATGTG CTGCAGATAC AGGCGTTGGA

801    ACCTGCGTCT CAAAAACCAC TTGGTAGCAC AAATCGCTCA AAT
       TGGACGCAGA GTTTTTGGTG AACCATCGTG TTTAGCGAGT TTA
```

Construction of pEW13

Distribution of erucic acid levels in LEAR (mol% if fatty acids)

Distribution of erucic acid levels in 94-He-24 (mol% of fatty acids)

US 7,459,607 B2

OIL BIOSYNTHESIS

This application claims priority, under 35 U.S.C. § 371, to International Patent application No. PCT/GB02/04642, filed Oct. 11, 2002 and published in English as WO 03/033713 on Apr. 24, 2003, which claims priority to Great Britain Patent Application No. GB 0124574.5, filed Oct. 12, 2001.

FIELD OF THE INVENTION

The present invention relates to the production of commercially useful oil in plants. In particular, the invention provides a method for producing such oil in plants. Also provided are the plants or parts thereof from which the oil is derived, use of the plant, and the oil itself.

BACKGROUND OF THE INVENTION

Plants have long been a commercially valuable source of oil. Traditionally, plant oils were used for nutritional purposes. Recently, however, attention has focused on plant oils as sources of industrial oils, for example as replacements for, or improvements on, mineral oils. Given that oil seeds of commercially useful crops such as *Brassica napus* contain a variety of lipids (Hildish & Williams, "Chemical Composition of Natural Lipids", Chapman Hall, London, 1964), it is desirable to tailor the lipid composition to better suit our needs, for example using recombinant DNA technology (Knauf, TIBtech, February 1987, 40-47).

The production of commercially desirable specific oils in plants on a large scale is limited in two ways. Some plant species make oils with very high levels of essentially pure, specific fatty acids, but these species are unable to be grown in sufficient quantities and of sufficient yield to provide a commercially valuable product. Other plant species produce sufficient amounts of oil, but the oil has low levels of the specific desired fatty acids. Nevertheless, the field of oil modification in plants is wide and a number of different products have already been designed. Rape oil containing lauric acid has been marketed, and soybeans with modified levels of unsaturated fatty acids are available. In some cases the production of speciality oils seems to be straight-forward. In others, however, a number of unexpected complications have arisen which have hampered the production of plants capable of making some specific oils. For example, mutations in plant lipid synthesis genes are generally difficult to detect due to the pleiotrophic effects of mutations on plant hardiness and yield. Even if detected, proteins involved in pathways of interest have proved difficult to isolate due to their biochemical instability. Where regulation of such proteins has been successfully altered, results generally do not coincide with expectations, presumably due to the effect of multiple converging pathways. Examples of such problems relating to the production of *Arabidopsis* producing petroselinic acid are disclosed in Ohlrogge, 13th *International Symposium on Plant Lipids*, Seville, Spain: 219 & 801, (1998). Thus, there is considerable work yet to be done in achieving reliable, large-scale production of a range of commercially desirable oils.

Broadly speaking, there are two main approaches to altering the lipid content of an oil, which to date have been applied as alternatives. Firstly, plants may be modified to produce fatty acids which are foreign to the native plant. For example, rape may be modified to produce laureate which is not naturally produced by that plant. Secondly, the pattern and/or extent of incorporation of fatty acids into the glycerol backbone of a lipid may be altered.

Lipids are formed by the addition of the fatty acid moieties into the glycerol backbone by acyltransferase enzymes. There are three positions on the glycerol backbone at which fatty acids may be introduced. The acyltransferase enzymes which are specific for each position are hence referred to as 1-, 2-, and 3-acyltransferase enzymes respectively.

One of the aims of lipid engineering is to produce oils which are high in erucic (22:1) acid. Such oils are desirable for a number of reasons, in particular as replacements and/or substitutes for mineral oils, as described above. In the case of *Brassica napus* one of the most commercially important crops cultivated today, and other oil seed *Brassica* species, e.g. *Brassica juncea*, the 2-acyltransferase positively discriminates against the incorporation of erucic acid in the second position. Thus, even in those crops where erucic acid is incorporated into the first and third positions, only a maximum of 66% of the fatty acids of the lipid can be erucic acid. These latter varieties of rape are nevertheless known as HEAR (high erucic acid rape) varieties.

It is desirable to further increase the erucic acid content of both HEAR varieties, and other useful vegetable oil crops, for example maize, sunflower, soya, mustards and linseed. Genes encoding 2-acyltransferases have been introduced into plants, in order to try to incorporate erucic acid into the second position of the glycerol backbone, with the aim of increasing the overall erucic acid content in a lipid (Brough et al., *Mol Breeding* 2: 133-142 (1996)). This was successful in the redistribution of erucic acid in the triglyceride but has not increased the overall erucic acid content of the oil. One possible reason for this is that the levels of "free" erucic acid available for incorporation into lipids in a plant are too low to support high levels of trierucin synthesis (Millar et al., *The Plant J.* 12(1) 121-131 (1997)). Thus, knowledge of the factors involved in the regulation of erucic acid levels in a plant is being sought.

In this text, the terms "free" or "available" erucic acid mean erucic acid which has not been incorporated into lipid. References to the erucic acid content of oil means that which has been incorporated into lipid.

Biochemical and genetic studies have elucidated most of the pathways involved in the production of vegetable oils (Ohlrogge & Browse, Plant Cell 7: 957-970, 1995). An enzyme involved in the synthesis of fatty acids is the fatty acid elongation enzyme (FAE) complex, also referred to as an elongase. This enzyme complex is responsible for the conversion of fatty acids 18 carbons long, such as oleic (18:1) acid, to fatty acids known as very long chain fatty acids, which include erucic acid (22:1). Given its involvement in the production of erucic acid, it is apparent that the elongase plays a role in regulation of the levels of free erucic acid in a plant. Thus, it has been suggested that, in relation to *Arabidopsis*, over-expression of the FAE1 gene may assist in obtaining higher levels of free erucic acid (Millar et al., *The Plant J.* 12(1) 121-131 (1997)). Depending upon the plant species, the products of this enzyme are C20 and C22 saturated fatty acids, utilised in wax production in leek, or C20 to C24 monounsaturated fatty acids utilised as seed storage oils in crucifers.

Over recent years, a number of β-keto-acyl-CoA synthetase ("elongase") genes, in addition to the *Arabidopsis* FAE1 gene, have been cloned from a variety of species. Sequence data is available for elongases isolated from *Arabidopsis* (Millar & Kunst, *Plant J.* 12: 121-131, (1997)), jojoba (Lassner et al, *Plant Cell* 8: 281-292, (1996)), honesty (Millar & Kunst, *Plant J.* 12: 121-131, (1997)), leek (Evenson & Post-Beittenmiller, *Plant Physiol.* 109: 707-716, (1995)) and oilseed rape (Sequence: Genbank AF009563 &

BNU50771). These enzymes all produce a range of other very long chain fatty acids besides erucic acid, for example fatty acid 20:1 in *Arabidopsis* and oilseed rape, fatty acids 20:0 and 22:0 in leek and fatty acid 24:1 in honesty and jojoba.

Recently, experiments have been performed on high-erucic acid rapeseed plants in which the plants were transformed with constructs encoding an acyltransferase and an elongase. However, none of the transformants were found to contain erucic acid levels greater than 60% (Han et al., *Plant Mol. Bio.* 46 229-239 (2001)).

SUMMARY OF THE INVENTION

The present invention aims to overcome or ameliorate the above problems of the prior art by enabling for the first time the production of lipid with higher levels of erucic acid.

Thus, in a first aspect of the present invention, there is provided a method of producing, in a plant, oil containing more than 66% erucic acid, wherein the method comprises (i) expressing in the plant nucleic acid encoding an elongase and nucleic acid encoding an acyltransferase; and (ii) extracting oil from the plant.

The present invention is based upon the inventors' discovery that the combination of an elongase enzyme and an acyltransferase enzyme expressed in a plant can have the surprising effect of increasing the erucic acid content of oil to above the theoretical maximum of 66%. These results mean that for the first time it has been possible to introduce erucic acid into all three positions in the glycerol backbone in at least a portion of the lipid of the oil and also cause an overall increase in the erucic acid incorporated into lipid rather than merely redistributing the erucic acid on the glycerol backbone. Thus, for the first time the invention enables the production of oil containing above 66% erucic acid in an ergonomic and agronomic fashion. The resulting oil can be used in a variety of industrial applications, such as feedstock's for surfactants, plasticisers, and surface coatings.

The nucleic acid sequences of the invention may be DNA or RNA, or any other option. The nucleic acid may be recombinant or isolated.

The elongase enzyme expressed in the plant is preferably one capable of the production of very long chain fatty acids including erucic acid, most preferably specific for the production of erucic acid. Examples of preferred elongase enzymes are *Brassica napus* FAE1-1 and FAE1-2 of FIGS. 1 and 2 respectively, or elongase enzymes encoded by the *B. napus* cDNA sequeneces disclosed in WO96/13582, or encoded by the *B. napus* sequences Genbank accession nos. AF009563 and BNU50771, or similar enzymes from other *Brassica* species, *Arabidopsis* (Millar & Kunst, Plant J, 12: 121-131, (1997), jojoba (Lassner et al, *Plant Cell* 8: 281-292, (1996)), Lunaria (Millar & Kunst, *Plant J.* 12: 121-131, (1997)) and *Nasturtium* (WO95/15387). Also included for use in the present invention are enzymes which are substantially identical in sequence to the elongases of FIG. 1 and/or FIG. 2, and which share the same enzyme activity as one or more of the elongases mentioned above.

The acyltransferase enzyme to be expressed in the plant may be a 1-, 2-, or 3-acyltransferase, but most preferably is a 2-acyltransferase, and is therefore capable of introducing a fatty acid into the second position of the glycerol backbone. More preferably, the 2-acyltransferase is capable of introducing erucic acid into the glycerol backbone. Examples of suitable 2-acyltransferase enzymes include those from *Limnanthes alba* (WO95/27791), *Limnanthes douglassi* (WO96/24674 and WO96/09394). Also included are acyltransferases which are substantially identical thereto, and which share the same enzyme activity as one or more of the acyltransferases mentioned above.

BRIEF DESCRIPTION OF THE DRAWINGS

The invention will now be described by way of non-limiting examples, with reference to the drawings in which:

FIG. 1 shows the nucleic acid sequence encoding the *Brassica napus* enzyme FAE1-1 (SEQ ID NO:1).

FIG. 2 shows the nucleic acid sequence encoding the *Brassica napus* enzyme FAE1-2 (SEQ ID NO:2).

FIG. 3 shows the nucleic acid sequence encoding the 2-acyltransferase of *Limnanthes douglasii* (SEQ ID NO:3).

DESCRIPTION OF THE INVENTION

Figure 4:
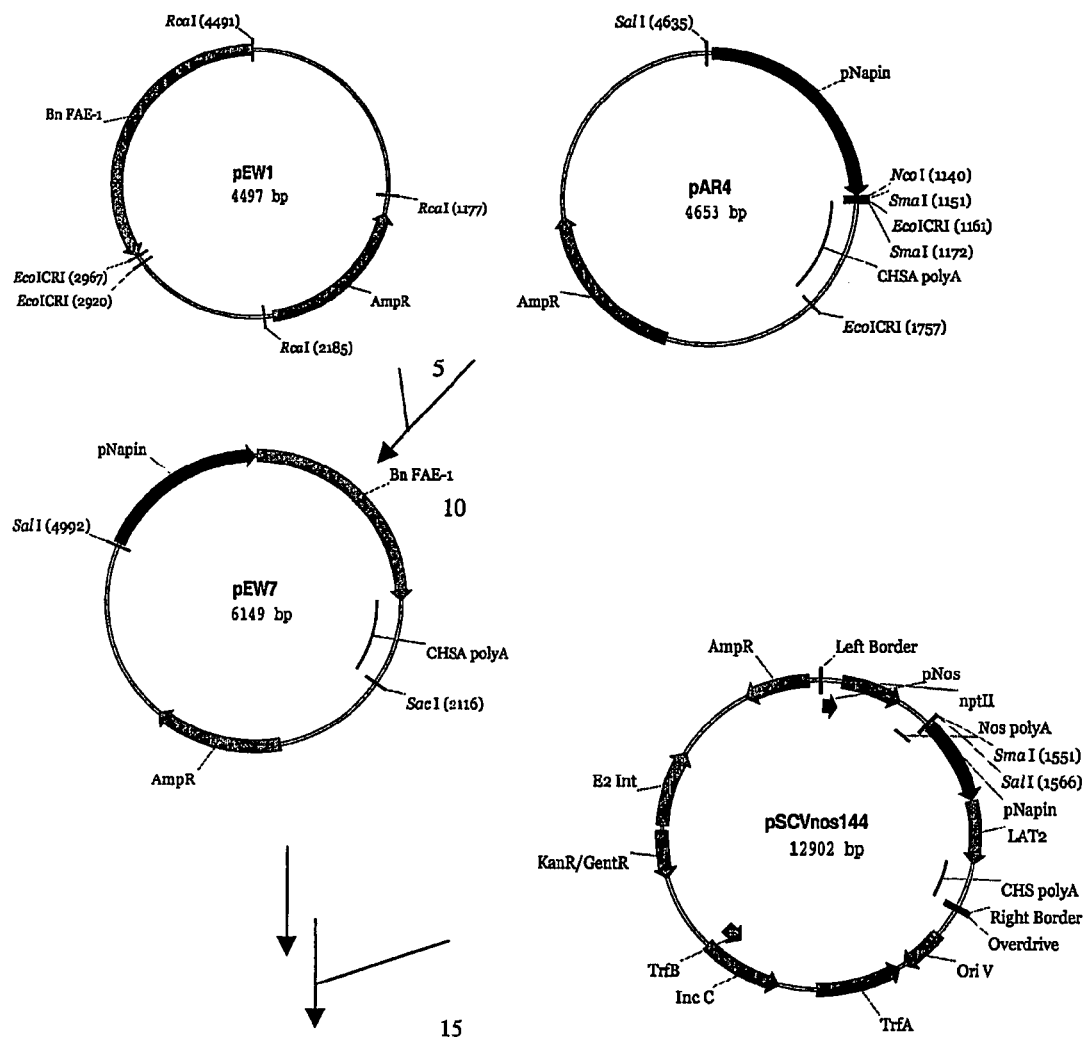
FIG. 4 shows the construction of plasmid pEW13.
Figure 4:
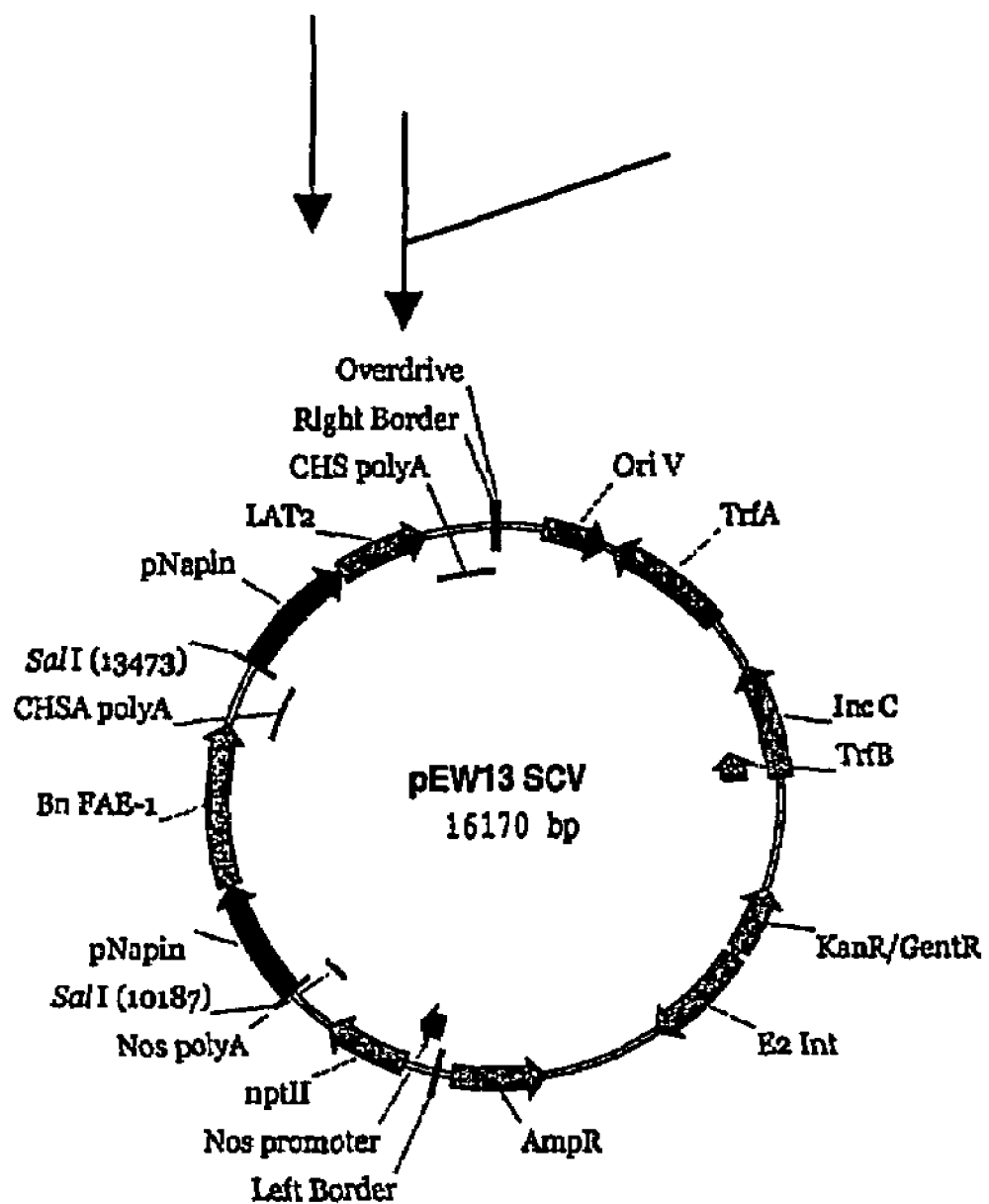

In the context of the present invention the term "substantially identical" means that the sequence has at least 50% sequence identity, desirably at least 75% sequence identity and more desirably at least 90 or at least 95% sequence identity with one or more of the above mentioned sequences. In some cases the sequence identity may be 99% or above.

"% identity", as known in the art, is a measure of the relationship between two polypeptide sequences or two polynucleotide sequences, as determined by comparing their sequences. In general, the two sequences to be compared are aligned to give a maximum correlation between the sequences. The alignment of the two sequences is examined and the number of positions giving an exact amino acid or nucleotide correspondence between the two sequences determined, divided by the total length of the alignment and multiplied by 100 to give a % identity figure. This % identity figure may be determined over the whole length of the sequences to be compared, which is particularly suitable for sequences of the same or very similar length and which are highly homologous, or over shorter defined lengths, which is more suitable for sequences of unequal length or which have a lower level of homology.

Methods for comparing the identity of two or more sequences are well known in the art. Thus for instance, programs available in the Wisconsin Sequence Analysis Package, version 9.1 (Devereux J et al, Nucleic Acids Res. 12:387-395, 1984, available from Genetics Computer Group, Maidson, Wis., USA), for example the programs BESTFIT and GAP, may be used to determine the % identity between two polynucleotides and the % identity between two polypeptide sequences. BESTFIT uses the "local homology" algorithm of Smith and Waterman (Advances in Applied Mathematics, 2:482-489, 1981) and finds the best single region of similarity between two sequences. BESTFIT is more suited to comparing two polynucleotide or two polypeptide sequences which are dissimilar in length, the program assuming that the shorter sequence represents a portion of the longer. In comparison, GAP aligns two sequences finding a "maximum similarity" according to the algorithm of Neddleman and Wunsch (J. Mol. Biol. 48:443-354, 1970). GAP is more suited to comparing sequences which are approximately the same length and an alignment is expected over the entire length. Preferably, the parameters "Gap Weight" and "Length Weight" used in each program are 50 and 3 for polynucleotide sequences and 12 and 4 for polypeptide sequences, respectively. Preferably, % identities and similarities are determined when the two sequences being compared are optimally aligned.

Other programs for determining identity and/or similarity between sequences are also known in the art, for instance the BLAST family of programs (Altschul S. F. et al, J. Mol. Biol., 215:403-410, 1990, Altschul S. F. et al, Nucleic Acids Res., 25:289-3402, 1997, available from the National Center for Biotechnology Information (NCB), Bethesda, Md., USA and accessible through the home page of the NCBI) and FASTA (Pearson W. R. and Lipman D. J., Proc. Nat. Acac. Sci., USA, 85:2444-2448, 1988, available as part of the Wisconsin Sequence Analysis Package). Preferably, the BLOSUM62 amino acid substitution matrix (Henikoff S. and Henikoff J. G., Proc. Nat. Acad. Sci., USA, 89:10915-10919, 1992) is used in polypeptide sequence comparisons including where nucleotide sequences are first translated into amino acid sequences before comparison.

Preferably, the program BESTFIT is used to determine the % identity of a query polynucleotide or a polypeptide sequence with respect to a polynucleotide or a polypeptide sequence of the present invention, the query and the reference sequence being optimally aligned and the parameters of the program set at the default value.

Preferably, the elongase and/or acyltransferase enzyme used in the present invention will not be native to the plant (i.e. the enzyme will be foreign to the plant). Thus, the nucleic acid encoding the foreign enzymes may be referred to as a transgene. The plant hosting the nucleic acid encoding the foreign enzyme(s) will therefore be transgenic. Such a plant may be readily distinguished from native plants due to the presence of foreign genetic material which would not be found in the native, non-transgenic plant, for example, vector sequences, marker genes, and multiple copies of nucleic acid encoding one or both of the above enzymes.

The transgene may encode an enzyme which is not present in the native, non-transformed plant, for example the 2-acyltransferase able to incorporate erucic acid at position 2 encoded by lat2 is not present in native, non-transformed *Brassica napus*. In such case a transgenic plant may be distinguished from a native, non-transformed plant by an assay for the foreign enzyme activity or by the presence of the reaction product (in this example trierucin). As the *Limnanthes* gene encoding lat2 is not present in native, non-transformed *Brasica napus*, a transgenic plant may also be distinguished from a native, non-transformed plant by testing for the presence of the lat2 gene sequence e.g. by PCR or Southern blot.

Alternatively the transgene may encode an enzyme which is already found in native, non-transformed plants, for example the elongase enzymes encoded by BnFAE1-1 and BnFAE1-2 are found in non-transformed *Brassica napus* (because this is the plant from which the genes were isolated). In this case a transgenic plant may be identified by changed enzyme activity (e.g. level, timing) in comparison with a non-transformed plant. Presence of the transgene may be positively verified by PCR or hybridisation tests for the presence of nucleotide sequences which are known to be unique to the expression cassette containing the transgene.

Preferably, the nucleic acid sequences encoding the acyltransferase and/or elongase are expressed in the plant through the period of oil biosynthesis. This preferably includes at least the period during which the fatty acids are incorporated into the glycerol backbone, i.e. triacylglycerols are produced. It may also include the period during which very long chain fatty acids are produced, the period of oil accumulation in the plant, and/or the period of any oil modification. The timing of each of these stages of oil biosynthesis may be readily determined by a person skilled in the art using time-course experiments using well established biochemical methods, such as GLC (Gas Liquid Chromatography) and HPLC ELSD (Evaporative Light Scatter Detection) analysis on triglycerides. The precise temporal expression pattern of the nucleic acid sequences may be adjusted according to their role in the oil biosynthesis pathway. For example, it may be desirable to express the elongase enzyme prior to the start of oil biosynthesis, during the period of fatty acid synthesis, in order to effectively increase the amount of "free" erucic acid prior to its incorporation into lipid. Similarly, the acyltransferase enzyme may be best expressed during the period of triacylglycerol synthesis. Depending upon the degree of overlap between the different stages of oil biosynthesis, it may be preferable for the elongase and acyltransferase enzymes to be expressed at the same time. In a most preferred embodiment, the temporal expression patterns of the foreign enzymes will mimic those of the corresponding native enzymes of the plant.

In addition to conferring temporal specificity on the foreign enzymes, it may also be desirable to express them in a spatially specific manner, for example to reduce any adverse effects in parts of the plant not involved in oil biosynthesis. In a preferred embodiment, the elongase and/or acyltransferase enzymes are expressed in the seed of the host plant.

The desired temporal and spatial specificity may be conferred by the use of appropriate regulatory sequences to drive expression of the nucleic acid sequences encoding the elongase and acyltransferase enzymes. Use of these regulatory sequences will allow a tighter control of transgene expression and improved co-ordination with oil biosynthesis in seeds. This will enable potentiation of transgene activity whilst avoiding ectopic expression. Thus, in a preferred embodiment, the elongase and/or acyltransferase nucleic acid sequences to be expressed in the plant are under the control of one or more regulatory sequences capable of driving expression in a temporally and spatially specific manner. Depending upon the desired temporal and spatial specificity of the acyltransferase and elongase enzymes, it may be preferably to place each under the control of the same or separate regulatory sequences. Examples of suitable regulatory sequences include the oleosin promoter (Plant et al Plant Mol Biol 25(2) 193-205 (1994)), the 2S napin promoter (European patent No 0255278), and the FAE promoters of *Brassica napus* (Han et al., Plant Mol. Biol. 46 229-239 (2001)) and *Arabidopsis*

(Rossak et al., Plant Mol. Biol. 46 717-725 (2001)). The regulatory sequences which drive expression of the native elongase and acyltransferase enzymes in the plant may also be used. The nucleic acid sequence to be expressed may also comprise 3' polyadenylation sequences, for example the Chalcone Synthase polyadenylation termination signal sequence.

In achieving the desired levels of erucic acid in the oil of the transgenic plant, it may be useful to overexpress the transgenes. Thus, the expression level will be higher than that of the native enzyme during its active period. This may be achieved by placing the transgenes under the control of a strong promoter, such as the napin promotes. The FAE promoters of *Brassica napus* may also be suitable for overexpression of the transgenes.

Where the elongase or acyltransferase enzymes are foreign to the plant into which they are introduced, it may be desirable to down-regulate, or disrupt the function of, the corresponding native enzymes or gene products in the plant. For this purpose, antisense sequences of the native elongase or acyltransferase genes may be used to suppress the expression of the native enzymes. The RNA transcribed from the antisense DNA will be capable of binding to, and destroying the function of, a sense version of the RNA found native in the cell, thereby disrupting its function. For example, antisense acyltransferase may be used in a plant where the native 2-acyltransferase is not specific for very long chain fatty acids such as erucic acid. Preferably, the antisense sequences will be capable of hybridising to the native sequence under stringent conditions, as defined below.

It is not crucial for any such antisense sequence to be transcribed at the same time as the nucleic acid encoding the foreign acyltransferase and elongase. Antisense RNA will in general only bind when its sense complementary strand is present and so will only have its toxic effect at the appropriate time. Thus, any suitable plant promoter may be used, although it will preferably share the same spatial specificity as the native enzyme. Examples of suitable promoters include the napin promoter and the promoter of the lat2 gene from *limnanthes*.

In the context of the present invention "stringent conditions" are defined as those given in Plant genetic Transformation and Gene Expression: A Laboratory Manual, Ed. Draper et al 1988, Blackwell Scientific Publications, p 252-255, modified as follows: prehybridization, hybridization and washes at 55-65° C., final washes (with 0.5×SSC, 0.1% SDS) omitted.

Alternatively, ribozyme technology may be used to disrupt the expression of the native elongase and/or acyltransferase in the plant. Ribozymes are RNA "enzymes" capable of highly specific cleavage against a given target sequence (Haseloff and Gerlarch, Nature 334 585-591 (1988)).

The nucleic acid sequences to be expressed in the plant may be introduced in the form of a vector. Where nucleic acids encoding both an elongase and acyltransferase enzymes are to be introduced, it may be preferable to incorporate both into a single vector. The vector may be, for example, a phage, plasmid or cosmid.

The vector will preferably also include one or more marker genes to enable the selection of plant cells which have been successfully transformed. Examples of suitable marker genes include antibiotic resistance genes such as those conferring resistance to kanamycin, G418 and hygromycin (npt-II, hyg-B); herbicide resistance genes such as those conferring resistance to phosphinothricin and sulfonamide based herbicides (bar and suI respectively; EP-A-242246 and EP-A-0369637) and screenable markers such as beta-glucoronidase (GB2197653), luciferase and green fluorescent protein.

The marker gene is preferably controlled by a second promoter which allows expression in cells other than the seed, thus allowing selection of cells or tissue containing the marker at any stage of development of the plant. Preferred second promoters are the promoter of nopaline synthase gene of *Agrobacterium* and the promoter derived from the gene which encodes the 35S subunit of cauliflower mosaic virus (CaMV) coat protein. However, any other suitable second promoter may be used.

In order to assist the process of deregulation, it is preferred that the selectable marker gene is not present in the plant which is to be grown commercially. Various techniques for marker elimination are available, including co-transformation followed by segregation and selection of segregants having the gene of interest but lacking the marker gene.

Methods for introducing nucleic acid into a plant are known to persons skilled in the art, and include techniques such as by the use of a disarmed Ti-plasmid vector carried by *agrobacterium*, for example as described in EP-A-0116718 and EP-A-0270822. Alternatively, the nucleic acid may be introduced by way of a particle gun, directly into the plant cells. This method is preferred for example where the plant is a monocot.

The oil may be extracted from the mature seeds of the plant by any suitable means which will be known to persons skilled in the art. For example, the methods described in Wilmer et al J Plant Physiol 147 486-492 (1996)) are available for laboratory scale extraction. For larger scale extraction, standard crushing techniques as practised by the industry may be used.

In a second aspect of the present invention, there is provided a plant capable of producing oil having an erucic acid content above 66%. Preferably, the plant is transgenic, and includes nucleic acid encoding an elongase enzyme capable of the production of very long chain fatty acids, including erucic acid, and nucleic acid encoding a 2-acyltransferase. Most preferably, the transgenes are in accordance with those defined in the first aspect of the invention.

The transgenic plants of the second aspect may be used in the production of tailored oils, which differ from native oils of the plant. In the present invention, the oil of the transgenic plant will differ from that of the native plant in terms of the erucic acid content of its oil. In particular, the erucic acid content of the oil will be higher than that of the native plant, and most preferably, it will be above 66%.

In a preferred embodiment of the invention, one or more of the plants' native oil biosynthesis enzymes may be rendered inoperative.

Any plant may be used in the present invention. Preferred plants are those whose seeds are used in the production of oil, for example *Brassica napus*, other *Brassica*, mustards, or other cruciferous plants, sunflower, soya or maize.

Also provided are plant parts, such as material required for propagating, in particular seeds.

A whole plant can be regenerated from a single transformed plant cell. Thus, in a further aspect the present invention provides a transgenic plant cell including nucleic acid sequences encoding an elongase enzyme capable of the production of very long chain fatty acids, including erucic acid, and nucleic acid encoding a 2-acyltransferase. The regeneration can proceed by known methods (for *Brassica napus* see Moloney et al Plant Cell Reports 8 238-242, 1989).

In a third aspect of the invention, there is provided oil having an erucic acid content above 66%. Preferably, the oil is produced by a method of the first aspect. In a final aspect of the present invention, there is provided the use of such a transformed plant in the production of tailored oil.

Preferred features of the first aspect of the invention are for the other aspects *mutatis mutandis*.

EXAMPLES

Example 1

Isolation of BnFAE1-1 and BnFAE1-2 and Cloning into a Binary Vector

Starting Material

High erucic rape plants of a line BGRV2 were grown in the glasshouse to provide leaf material for DNA isolation. DNA was isolated essentially as described in Sambrook et al. (Molecular cloning: a laboratory manual, $2^{nd}$ ed., Cold Spring Harbor Laboratory Press, Cold Spring Harbor, N.Y., 1989).

PCR Amplification of BnFAE1 Sequences

Previously published *B. napus* fae1 sequences were analysed and two oligonucleotide primers were designed to amplify the *B. napus* fae1 genes from the high erucic acid winter line BGRV2:

```
                                                (SEQ ID NO:4)
    BnFAE-F
    5'CCTCATGACGTCCATTAACGTAAAGCTCC 3'
    and (SEQ ID NO:5)
    BnFAE-R
    5'GTGAGCTCTTATTAGGACCGACCGTTTGGG 3'.
```

PCR was performed using Tli Taq polymerase in the buffer supplied with 1.5 mM MgCl2, and an annealing temperature of 60° C. PCR products were cloned into pBluescriptII KS(+) (Stratagene) SmaI site and sequenced (MWG Biotech). (FIGS. 1 and 2)

The sequence of the BnFAE1-1 open reading frame shows higher homology to a published partial cDNA derived from *Brassica oleracea* than does BnFAE1-2. We therefore suggest that BnFAE1-1 represents the gene derived from the *B. oleracea* parent of *B. napus* (C-genome) and that BnFAE1-2 represents the *B. rapa* genome (A-genome).

Construction of Plasmids pEW13 and pEW14

The two fae1 genes which had been amplified, cloned into pBluescript II, and sequenced were designated as pEW1 (fae1-1) and pEW3 (fae1-2). The fae1 genes were transferred as RcaI-EcoICRI fragments into pAR4 (Biogemma UK) NcoI-SmaI sites to place the genes between the Pnapin and CHS polyA sequences (pEW7 and 6). The two fae1 expression cassettes were inserted adjacent to a similar Lat2 cassette, by digesting pEW7 and 6 with SalI-SacI and inserting the fragments into pT7Blue2 SalI-SacI sites (creating pEW9 and 8), before transfer of an EcoRI EcoICRI fragment into the binary vector pSCVnos144 (Biogemma UK) SalI-SmaI sites resulting in pEW13 and 14. The cloning strategy for the construction of pEW13 is shown in FIG. 4.

Example 2

BnFAE1 Genes Encode Elongase Activities which Specifically Catalyse the Formation Erucic Acid (22:1)

To demonstrate the product specificity of the two BnFAE1 genes, they were expressed in developing embryos of low erucic acid rape (LEAR).

Both plasmid pEW13 and plasmid pEW14 were transformed into *Agrobacterium* strain C58pMP90 and transformed into LEAR using agrobacterial transformation essentially as described in Moloney et al., (Plant Cell Reports 8: 238-242, 1989). Seed of the resulting transformed plants contain significant levels of erucic acid since both BnFAE1 genes complement mutations in the elongases of the LEAR line.

Oil extraction, separation, and analysis by GC was performed essentially as described in Wilmer et al (J. Plant Physiol. 147: 486-492, 1996). Oil was extracted from samples of 20 seed from each self-pollinated transformed plant. Seed were extacted with 1 ml chloroform, 2.8 ml methanol/0.01 N hydrochloric acid (1:0.8, by vol.), containing 2 mg/ml triheptadecanoin as an internal standard. After shaking, 1 ml chloroform and 1 ml 0.01N hydrochloric acid were added and mixed. The phases were separated by centrifugation in a bench-top centrifuge, and the aqueous phase washed with a further 1.5 ml chloroform. The organic fraction contains most lipids.

Triglycerides were purified on 0.25 mm Silica gel 60 TLC plates, developed in hexane:diethyl ether:acetic acid (70:30:1 by vol.). After drying the lipids were visualised with iodine vapour and areas containing triglycerides were scraped off. TAG were transmethylated to produce fatty acid methyl esters (FAMEs) which could be analysed by gas chromatography.

Figure 5:
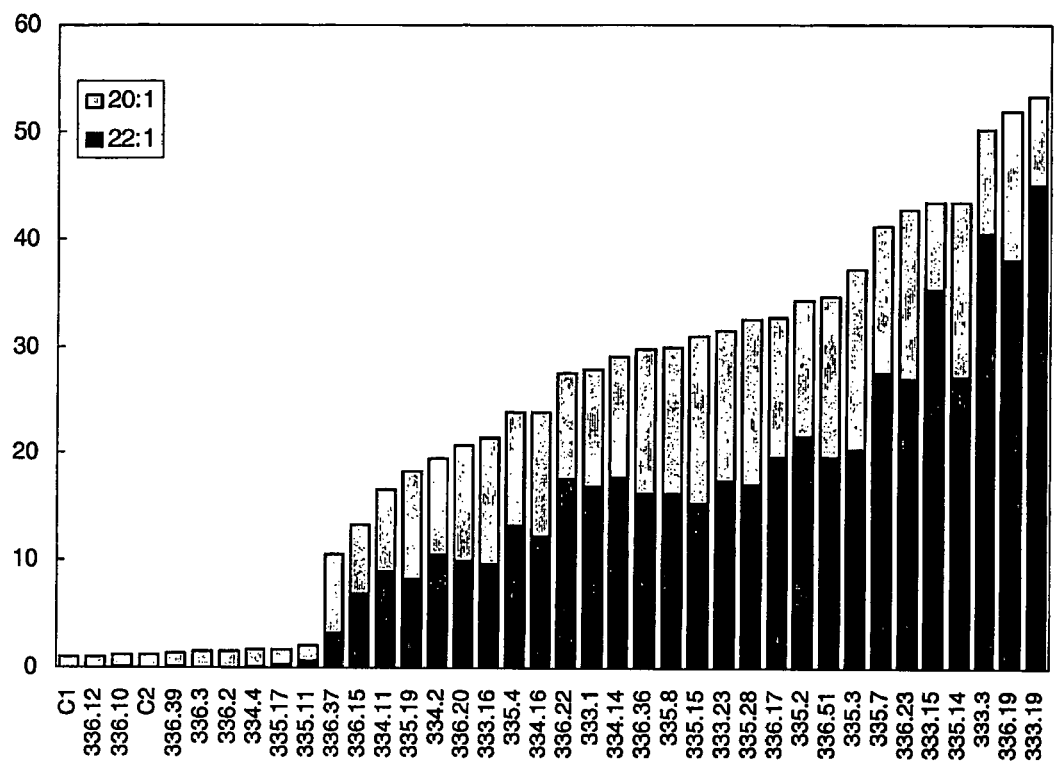
FIG. 5 shows the distribution of erucic acid levels, expressed as mol % of fatty acids, in seeds of LEAR transformants determined by gas chromatography (20:1=eicosenoic acid; 22:1=erucic acid). Transgenic lines designated 333.n and 334.n were transformed with constructs containing the fae1-1 gene; lines designated 335.n and 336.n were transformed with constructs containing the fae1-2 gene. Data are derived from single samples of 20 seeds.

FAME oil analysis was performed on mature seed of 11 plants transformed with constructs containing the fae1-1 gene and 25 plants transformed with constructs containing the fae1-2 gene demonstrating that the introduction of either fae1 gene led to a dramatic increase in the VLCFAs eicosenoic and erucic acid (C20:1 and C22:1) with a corresponding decrease in oleic acid (C18:1) (FIG. 5). Both fae1 genes functioned well in the production of VLCFAs.

Example 3

BnFAE1 Genes Encode Elongase Activities which Increase Erucic Acid Levels in High-erucic Acid Oilseed Rape A winter high-erucic acid line, BGRV2 was transformed with the two plasmids pEW13 and pEW14 previously tested in LEAR to examine whether the yield of erucic acid could be further enhanced in a cultivar which produced erucic acid.

Both plasmid pEW13 and plasmid pEW14 were transformed into *Agrobacterium* strain C58pMP90 and transformed into HEAR using agrobacterial transformation essentially as described in Moloney et al., (Plant Cell Reports 8: 238-242, 1989).

Oil analysis was performed on mature seed as described in Example 2.

Figure 6:
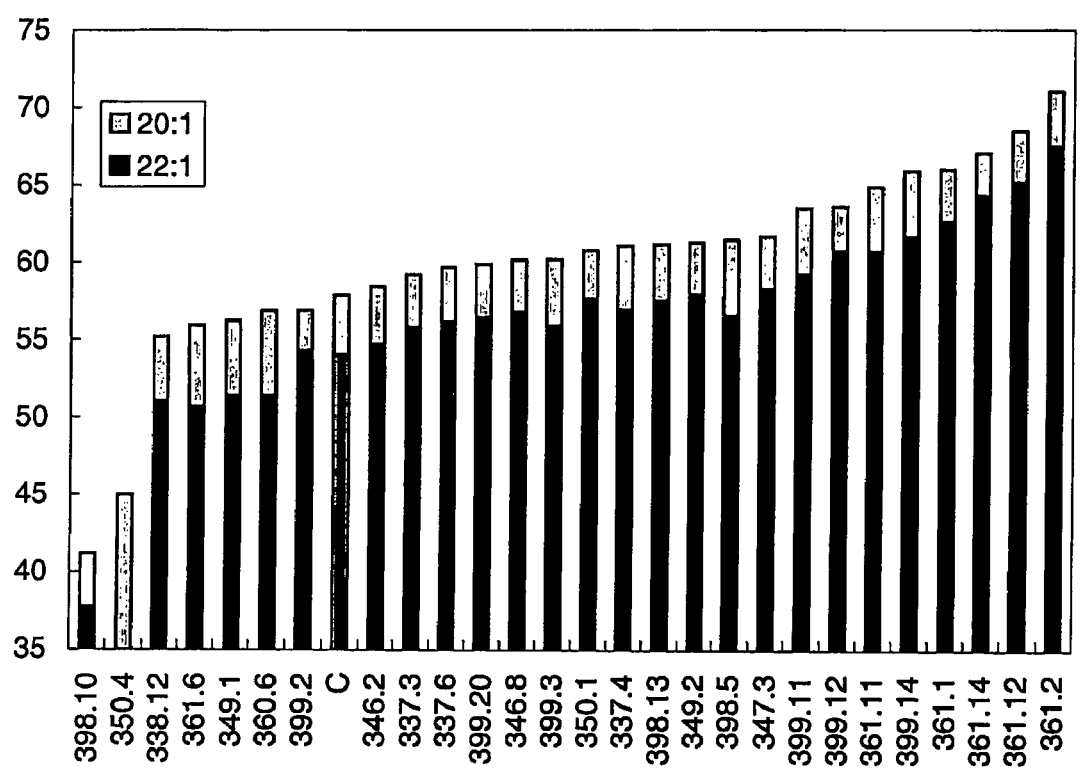
FIG. 6 shows the distribution of erucic acid levels, expressed as mol % of fatty acids, in seeds of high erucic acid winter cultivar BGRV2 transformants determined by gas chromatography (20:1=eicosenoic acid; 22:1=erucic acid). Transgenic lines were transformed with either pEW13 (fae1-1 plus lat2) (Lines 337.n, 346.n, 349.n, 360.n, 398.n, 399.n) or pEW14 (fae1-2 plus lat2) (Lines 338.n, 347.n, 350.n, 361.n). Data are derived from single samples of 20 seeds.

Twenty seven plants were analysed (10 with fae1-1 plus lat2, 17 with fae1-2 plus lat2), 9 of which showed an increase in erucic acid of at least 4 mol %, the highest with 67.5 mol % fatty acids compared to the control of 54% as shown in FIG. 6. Southern blot hybridisation of some of these plant lines showed that those with an increase in erucic acid had single or double insertions, whereas one of three lines which exhibited a considerable decrease (34%) contained 5 copies (data not shown), so that the phenotype observed could be due to co-suppression.

The data were applied to a t-test to determine whether there was a significant difference between the two populations of plants derived from fae1-1 or fae1-2 plus lat2. The probability value p=0.00056917, demonstrated that there was a significant difference between the populations, and that fae1-2 appeared to be more efficient.

The construct pEW14 (fae1-2 plus lat2) was also used to transform a Canadian spring HEAR line BGRV40, with similar results. Three of the four transgenic plants produced, exhibited a considerable increase in erucic acid whereas one line was repressed.

In the lines derived from either of the HEAR varieties it is C22:1 which is specifically increased, not C20:1.

In all cases, it is the Ti generation that has been analysed, which is hemizygous. After self-fertilization and segregation analysis it will be possible to re-evaluate the erucic acid levels in the T2 generation, which may then exhibit further increases in C22:1 as the inserted T-DNA bearing the elongase and acyl-transferase cassette becomes homozygous.

Sn-2 analysis confirmed the incorporation of C22:1 at the Sn-2 position of the TAG by the 2-acyltransferase encoded by the introduced lat2 gene.

Example 4

Very High Erucic Acid Levels are Stable in the next Generation in Oilseed Rape

Five lines of the winter high-erucic acid line, BGRV2, transformed with the plasmid pEW 14, and three lines of the spring high-erucic acid line, BGRV40, transformed with the plasmid pEW14, chosen from the material described in Example 3 were grown in a following generation.

Four of the winter high erucic-acid lines and two of the spring high-erucic acid lines contained one or two copies of the transgene as determined by southern analysis, whereas one each of the winter and spring lines contained multiple copies of the transgenes.

Twenty plants per line were grown in the glasshouse and presence of the additional fae1-2 gene was confirmed using PCR with a primer sequence internal to the fae1-2 sequence and a primer inside the CHS terminator sequence. Mature seed was collected for analysis and oil analysis was performed on these seed as described in Example 2.

Figure 7:
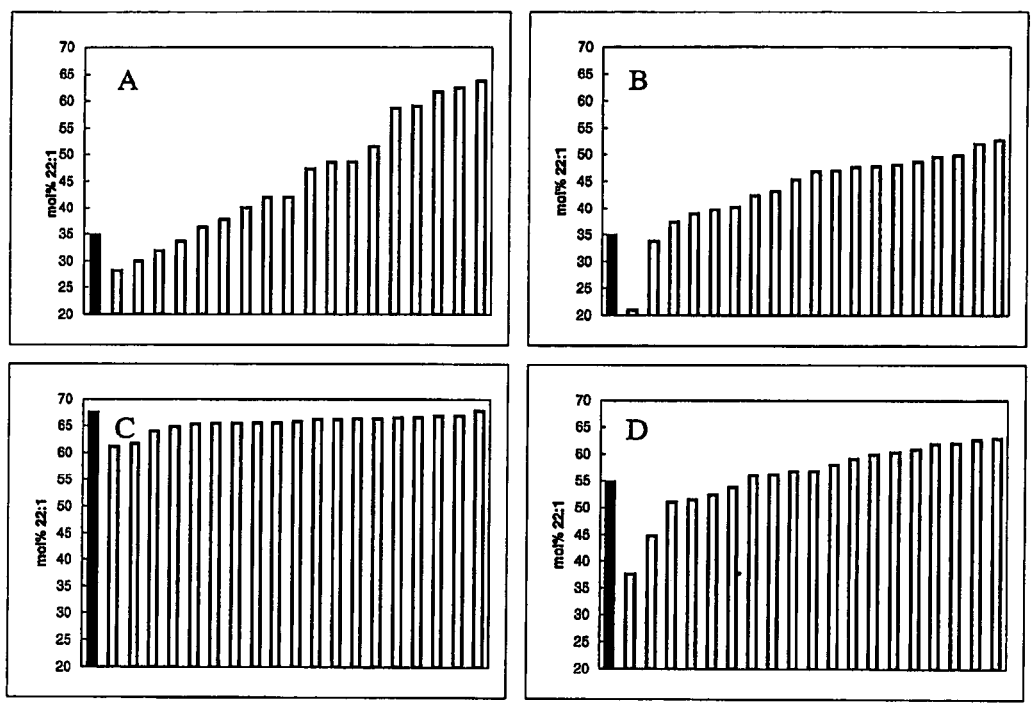
FIG. 7 shows the distribution of erucic acid content in selected progeny of primary transformed lines carrying the pEW14 transgenes. a: suppressed BGRV2 line in T1; suppressed BGRV40 line in T1; c: very high-erucic acid BGRV2 in T1; d: very high-erucic acid BGRV40 in T1. The black bar in each panel represents the T1 parent seed, white bars represent the progeny seed.

The two lines with multiple copies of the transgene that showed reduced levels of erucic acid in the T1 seed, both produced a wide range of erucic levels in the T2, as shown in FIG. 7.a and b. The lowest levels observed were below those observed in T1 seed, the highest levels well above the level of erucic acid observed in non-transgenic control oilseed rape of the appropriate line, and similar to the highest levels observed in the low-copy number lines, at least for the winter oilseed rape.

For the lines that showed increases in erucic acid in the T1 seed, this phenotype was maintained in the T2 seed, with the highest levels of erucic acid observed still around 67 to 68% (FIG. 7.c and d).

When the progeny of the lines with single or double copies of the transgene were tested by PCR for the presence of the transgene, segregation ratios of transgenic versus non-transgenic plants were observed that are consistent with a mendelian segregation of the transgene. Chi-square tests returned values showing non-significant deviation from an independent segregation model (data not shown).

The invention claimed is:

1. A method of producing oil in a high erucic acid *Brassica napus* plant, the method comprising (i) expressing in the plant a nucleic acid encoding an elongase and a nucleic acid encoding an 2-acyltransferase enzyme; and (ii) extracting oil from the plant, wherein said elongase is a *Brassica napus* FAE1-2 elongase encoded by SEQ ID NO: 2.

2. The method according to claim 1, wherein the 2-acyltransferase is from *L. douglassi*.

3. The method according to claim 1, wherein the nucleic acid sequences are under the control of a regulatory sequence.

4. The method according to claim 3, wherein the regulatory sequence is a FAE promoter of *Brassica napus*.

5. The method according to claim 1, wherein the nucleic acid sequences are provided in the form of a vector.

6. The method according to claim 1, wherein the nucleic acid sequences are operably linked to one or more marker genes.

7. The method according to claim 1, wherein the activity of the native elongase and/or acyltransferase of the plant is suppressed.

8. The method according to claim 7, wherein the activity is suppressed by antisense technology.

9. A transgenic *Brassica napus* plant from a high erucic acid *Brassica napus* plant line, wherein said plant comprises, as transgenes, a nucleic acid encoding an elongase and a nucleic acid encoding a 2-acyltransferase enzyme, and expresses said 2-acyltransferase and said elongase enzyme, wherein said elongase is a FAE1-2 elongase encoded by SEQ ID NO: 2.

10. A seed of the *Brassica napus* plant of claim 9 wherein said seed contains, as transgenes, a nucleic acid encoding an elongase and a nucleic acid encoding an 2-acyltransferase enzyme, wherein said elongase is a FAE1-2 elongase encoded by SEQ ID NO: 2.

* * * * *

SEQUENCE LISTING

<160> NUMBER OF SEQ ID NOS: 5

<210> SEQ ID NO 1
<211> LENGTH: 1521
<212> TYPE: DNA
<213> ORGANISM: Brassica napus

<400> SEQUENCE: 1

```
atgacgtcca ttaacgtaaa gctcctttac cattacgtca taaccaacct tttcaacctt      60
tgtttctttc cattaacggc gatcgtcgcc ggaaaagcct atcggcttac catagacgat     120
cttcaccact tatactattc ctatctccaa cacaacctca taaccattgc tccactcttt     180
gccttcaccg ttttcggttc ggttctctac atcgcaaccc ggcccaaacc ggtttacctc     240
gttgagtact catgctacct tccaccaacg cattgtagat caagtatctc caaggtcatg     300
gatatctttt accaagtaag aaaagctgat ccttctcgga acggcacgtg cgatgactcg     360
tcctggcttg acttcttgag gaagattcaa gaacgttcag gtctaggcga tgaaacccac     420
gggcccgagg ggctgcttca ggtccctccc cggaagactt ttgcggcggc gcgtgaagag     480
acggagcaag ttatcattgg tgcgctagaa aatctattca agaacaccaa tgttaaccct     540
aaagatatag gtatacttgt ggtgaactca agcatgttta atccaactcc ttcgctctcc     600
gcgatggtcg ttaacacttt caagctccga agcaacgtaa gaagctttaa ccttggtggc     660
atgggttgta gtgccggcgt tatagccatt gatctagcaa aggacttgtt gcatgtccat     720
```

```
aaaaatacgt atgctcttgt ggtgagcaca gagaacatca cttataacat ttacgctggt      780
gataataggt ccatgatggt ttcaaattgc ttgttccgtg ttggtggggc cgctattttg      840
ctctccaaca agcctagaga tcgtagacgg tccaagtacg agctagttca cacggttcga      900
acgcataccg gagctgacga caagtctttt cgttgcgtgc aacaaggaga cgatgagaac      960
ggcaaaaccg gagtgagttt gtccaaggac ataaccgatg ttgctggtcg aacggttaag     1020
aaaaacatag caacgctggg tccgttgatt cttccgttaa gcgagaaact tctttttttc     1080
gttaccttca tgggcaagaa acttttcaaa gacaaaatca acattatta cgtcccggac     1140 ttcaagcttg ctatcgacca ttttttgtata catgccggag gcaaagccgt gattgatgtg    1200
ctagagaaga acctaggcct agcaccgatc gatgtagagg catcaagatc aacgttacat     1260
agatttggaa acacttcatc tagctcaata tggtatgagt tggcatacat agaagcaaaa     1320
ggaaggatga agaaaggtaa taaagtttgg cagattgctt tagggtcagg ctttaagtgt     1380
aacagtgcag tttggtggc tctaaacaat gtcaaagctt caacaaatag tccttgggaa      1440
cactgcatcg acagataccc ggttaaaatt gattctgatt caggtaagtc agagactcgt     1500
gtccaaaacg gtcggtccta a                                                1521

<210> SEQ ID NO 2
<211> LENGTH: 1521
<212> TYPE: DNA
<213> ORGANISM: Brassica napus

<400> SEQUENCE: 2
atgacgtcca ttaacgtaaa gctcctttac cattacgtca taaccaaccct tttcaacctt     60 tgcttctttc cgttaacggc gatcgtcgcc ggaaaagcct atcggcttac catagacgat     120
cttcaccact tatactattc ctatctccaa cacaacctca taaccatcgc tccactcttt     180
gccttcaccg ttttcggttc ggttctctac atcgcaaccc ggcccaaacc ggtttacctc     240
gttgagtact catgctacct tccaccaacg cattgtagat caagtatctc caaggtcatg     300
gatatctttt atcaagtaag aaaagctgat ccttctcgga acggcacgtg cgatgactcg     360
tcgtggcttg acttcttgag gaagattcaa gaacgttcag gtctaggcga tgaaactcac     420
gggcccgagg ggctgcttca ggtccctccc cggaagactt tgcggcggc gcgtgaagag     480 acggagcaag ttatcattgg tgcactagaa aatctattca agaacaccaa cgttaaccct     540
aaagatatag gtatacttgt ggtgaactca agcatgttta atccaactcc atcgctctcc     600
gcgatggtcg ttaacacttt caagctccga agcaacgtaa gaagctttaa ccttggtggc     660
atgggttgta gtgccggcgt tatagccatt gatctagcaa aggacttgtt gcatgtccat     720
aaaaatacgt atgctcttgt ggtgagcaca gagaacatca cttataacat ttacgctggt     780
gataataggt ccatgatggt ttcaaattgc ttgttccgtg ttggtggggc cgctattttg     840
ctctccaaca agcctggaga tcgtagacgg tccaagtacg agctagttca cacggttcga     900
acgcataccg gagctgacga caagtctttt cgttgcgtgc aacaaggaga cgatgagaac     960
ggcaaaatcg gagtgagttt gtccaaggac ataaccgatg ttgctggtcg aacggttaag    1020
aaaaacatag caacgttggg tccgttgatt cttccgttaa gcgagaaact tctttttttc    1080
gttaccttca tgggcaagaa acttttcaaa gataaaatca acattacta cgtcccggat    1140 ttcaaacttg ctattgacca ttttttgtata catgccggag gcagagccgt gattgatgtg    1200
ctagagaaga acctagccct agcaccgatc gatgtagagg catcaagatc aacgttacat    1260
```

```
agatttggaa acacttcatc tagctcaata tggtatgagt tggcatacat agaagcaaaa    1320
ggaaggatga agaaaggtaa taaagtttgg cagattgctt tagggtcagg ctttaagtgt    1380
aacagtgcag tttgggtggc tctaaacaat gtcaaagctt cgacaaatag tccttgggaa    1440
cactgcatcg acagataccc ggtcaaaatt gattctgatt caggtaagtc agagactcgt    1500
gtccaaaacg gtcggtccta a                                              1521

<210> SEQ ID NO 3
<211> LENGTH: 843
<212> TYPE: DNA
<213> ORGANISM: Brassica napus

<400> SEQUENCE: 3
atggccaaaa ctagaactag ctctctccgc aacaggagac aactaaagcc ggctgtagct      60
gctactgctg atgatgataa agatgggggtt tttatggtat tgctatcgtg ttttaaaatt    120
tttgtttgct ttgccatagt gttgatcacc gcggtggcat ggggactaat catggtcttg    180
ctcttacctt ggccttatat gaggattcga ctaggaaatc tatacggcca tatcattggt    240
ggattagtga tatggatttta cggaatacca ataaagatcc aaggatccga gcatacaaag    300
aagagggcca tttatataag caatcatgca tctcctatcg atgctttctt tgttatgtgg    360
ttggctccca taggcacagt tggtgttgca agaaagagg ttatatggta tccgctgctt    420
ggacaactat atacattagc ccatcatatt cgcatagatc ggtcaaaccc ggctgcggct    480
attcagtcta tgaaagaggc agttcgtgta ataaccgaaa agaatctctc tctgattatg    540
tttccagagg gaaccaggtc gagagatggg cgtttacttc ctttcaagaa gggttttgtt    600
catctagcac ttcagtcaca tctcccaata gttccgatga tccttacagg tacacattta    660
gcatggagga aaggtacctt ccgtgtccgg ccagtaccca tcactgtcaa gtaccttcct    720
cctataaaca ctgatgattg gactgttgac aaaatcgacg attacgtcaa aatgatacac    780
gacgtctatg tccgcaacct acctgcgtct caaaaaccac ttggtagcac aaatcgctca    840
aat                                                                  843

<210> SEQ ID NO 4
<211> LENGTH: 29
<212> TYPE: DNA
<213> ORGANISM: Artificial Sequence
<220> FEATURE:
<223> OTHER INFORMATION: BnFAE-F oligonucleotide primer

<400> SEQUENCE: 4
cctcatgacg tccattaacg taaagctcc                                       29

<210> SEQ ID NO 5
<211> LENGTH: 30
<212> TYPE: DNA
<213> ORGANISM: Artificial Sequence
<220> FEATURE:
<223> OTHER INFORMATION: BnFAE-R oligonucleotide primer

<400> SEQUENCE: 5
gtgagctctt attaggaccg accgtttggg                                      30
```